United States Patent
Mayumi

(10) Patent No.: US 11,019,292 B2
(45) Date of Patent: May 25, 2021

(54) IMAGER AND IMAGING DEVICE

(71) Applicant: FUJIFILM Corporation, Tokyo (JP)

(72) Inventor: Kazuya Mayumi, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/999,023

(22) Filed: Aug. 20, 2020

(65) Prior Publication Data

US 2020/0382729 A1 Dec. 3, 2020

Related U.S. Application Data

(63) Continuation of application No. PCT/JP2019/006604, filed on Feb. 21, 2019.

(30) Foreign Application Priority Data

Feb. 22, 2018 (JP) .............................. JP2018-030137

(51) Int. Cl.
  *H04N 5/369* (2011.01)
  *A61B 1/05* (2006.01)
  *H04N 5/217* (2011.01)
  *H01L 27/146* (2006.01)

(52) U.S. Cl.
  CPC ............ *H04N 5/369* (2013.01); *A61B 1/051* (2013.01); *H04N 5/2178* (2013.01); *H01L 27/14643* (2013.01)

(58) Field of Classification Search
  CPC ...................................................... H04N 5/369
  USPC ......................................................... 348/294
  See application file for complete search history.

(56) References Cited

U.S. PATENT DOCUMENTS

| 2004/0069998 A1 | 4/2004 | Harazono |
| 2006/0017128 A1 | 1/2006 | Harazono |
| 2011/0075003 A1* | 3/2011 | Suzuki .................. H04N 9/045 348/311 |

(Continued)

FOREIGN PATENT DOCUMENTS

| CN | 1423477 | 6/2003 |
| CN | 103378119 | 10/2013 |

(Continued)

OTHER PUBLICATIONS

"International Search Report (Form PCT/ISA/210) of PCT/JP2019/006604," dated May 14, 2019, with English translation thereof, pp. 1-3.

(Continued)

*Primary Examiner* — Joel W Fosselman
(74) *Attorney, Agent, or Firm* — JCIPRNET

(57) ABSTRACT

An imager includes: an imaging sensor chip; a fixing member to which the imaging sensor chip is fixed, and which is electrically connected to the imaging sensor chip and has a first linear expansion coefficient; and a circuit board that is fixed to the fixing member via a conductive member, the circuit board comprises a first member having the first linear expansion coefficient and a second member having a second linear expansion coefficient smaller than the first linear expansion coefficient and larger than a linear expansion coefficient of a semiconductor substrate forming the imaging sensor chip, and a content of the second member in the back side portion is greater than a content of the second member in the front side portion.

13 Claims, 6 Drawing Sheets

(56) References Cited

U.S. PATENT DOCUMENTS

2013/0286565 A1   10/2013   Tsuduki et al.
2018/0040584 A1   2/2018    Kang

FOREIGN PATENT DOCUMENTS

| JP | 2001127200 | 5/2001 |
| JP | 2002100704 | 4/2002 |
| JP | 2009094168 | 4/2009 |
| JP | 2011066091 | 3/2011 |
| JP | 2013243339 | 12/2013 |
| JP | 2014170819 | 9/2014 |
| JP | 2017183386 | 10/2017 |

OTHER PUBLICATIONS

"Written Opinion of the International Searching Authority (Form PCT/ISA/237) of PCT/JP2019/006604," dated May 14, 2019, with English translation thereof, pp. 1-7.
"International Preliminary Report on Patentability (Form PCT/IB/373) of PCT/JP2019/006604," dated Aug. 27, 2020, with English translation thereof, pp. 1-8.
"Office Action of China Counterpart Application", dated Jan. 6, 2021, with English translation thereof, p1-p10.

* cited by examiner

FIG. 5

| REFERENCE | MATERIAL | CONTENT (%) |
|---|---|---|
| CONDUCTIVE LAYER 51t | TUNGSTEN | 10 |
| INSULATING LAYER 51s | CERAMIC | |
| CONDUCTIVE LAYER 52t | TUNGSTEN | 10 |
| INSULATING LAYER 52s | CERAMIC | |
| CONDUCTIVE LAYER 53t | TUNGSTEN | 10 |
| INSULATING LAYER 53s | CERAMIC | |
| CONDUCTIVE LAYER 54t | TUNGSTEN | 10 |
| INSULATING LAYER 54s | CERAMIC | |
| CONDUCTIVE LAYER 55t | TUNGSTEN | 15 |
| INSULATING LAYER 55s | CERAMIC | |
| CONDUCTIVE LAYER 56t | TUNGSTEN | 15 |
| INSULATING LAYER 56s | CERAMIC | |
| CONDUCTIVE LAYER 57t | TUNGSTEN | 15 |
| INSULATING LAYER 57s | CERAMIC | |
| CONDUCTIVE LAYER 58t | TUNGSTEN | 15 |

FIG. 6

| REFERENCE | MATERIAL | CONTENT (%) |
|---|---|---|
| CONDUCTIVE LAYER 51t | TUNGSTEN | 11.25 |
| INSULATING LAYER 51s | CERAMIC | |
| CONDUCTIVE LAYER 52t | TUNGSTEN | 11.25 |
| INSULATING LAYER 52s | CERAMIC | |
| CONDUCTIVE LAYER 53t | TUNGSTEN | 11.25 |
| INSULATING LAYER 53s | CERAMIC | |
| CONDUCTIVE LAYER 54t | TUNGSTEN | 11.25 |
| INSULATING LAYER 54s | CERAMIC | |
| CONDUCTIVE LAYER 55t | TUNGSTEN | 13.75 |
| INSULATING LAYER 55s | CERAMIC | |
| CONDUCTIVE LAYER 56t | TUNGSTEN | 13.75 |
| INSULATING LAYER 56s | CERAMIC | |
| CONDUCTIVE LAYER 57t | TUNGSTEN | 13.75 |
| INSULATING LAYER 57s | CERAMIC | |
| CONDUCTIVE LAYER 58t | TUNGSTEN | 13.75 |

FIG. 7

| REFERENCE | MATERIAL | CONTENT (%) |
|---|---|---|
| CONDUCTIVE LAYER 51t | TUNGSTEN | 16.25 |
| INSULATING LAYER 51s | CERAMIC | |
| CONDUCTIVE LAYER 52t | TUNGSTEN | 16.25 |
| INSULATING LAYER 52s | CERAMIC | |
| CONDUCTIVE LAYER 53t | TUNGSTEN | 16.25 |
| INSULATING LAYER 53s | CERAMIC | |
| CONDUCTIVE LAYER 54t | TUNGSTEN | 16.25 |
| INSULATING LAYER 54s | CERAMIC | |
| CONDUCTIVE LAYER 55t | TUNGSTEN | 8.75 |
| INSULATING LAYER 55s | CERAMIC | |
| CONDUCTIVE LAYER 56t | TUNGSTEN | 8.75 |
| INSULATING LAYER 56s | CERAMIC | |
| CONDUCTIVE LAYER 57t | TUNGSTEN | 8.75 |
| INSULATING LAYER 57s | CERAMIC | |
| CONDUCTIVE LAYER 58t | TUNGSTEN | 8.75 |

IMAGER AND IMAGING DEVICE

CROSS REFERENCE TO RELATED APPLICATION

This is a continuation of International Application No. PCT/JP2019/006604 filed on Feb. 21, 2019, and claims priority from Japanese Patent Application No. 2018-030137 filed on Feb. 22, 2018, the entire disclosures of which are incorporated herein by reference.

BACKGROUND OF THE INVENTION

1. Field of the Invention

The present invention relates to an imager and an imaging device comprising the imager.

2. Description of the Related Art

Recently, there has been a rapid increase in demand for a device having an imaging function, such as a digital still camera, a digital video camera, a portable telephone such as a smartphone, a tablet terminal, and an electronic endoscope in accordance with an increase in resolution of an imaging sensor such as a charge coupled device (CCD) image sensor or a complementary metal oxide semiconductor (CMOS) image sensor. A device having an imaging function as described above is referred to as an imaging device.

The imaging device comprises an imager including an imaging sensor chip that is a semiconductor chip, a package that houses the imaging sensor chip, and a circuit board on which the package is mounted.

JP2002-100704A, JP2001-127200A, and JP2009-094168A disclose a structure of a unit including a semiconductor chip, a package that houses the semiconductor chip, and a circuit board on which the package is mounted.

SUMMARY OF THE INVENTION

In a case where the package that houses the semiconductor chip is mounted on the circuit board, the unit is placed in a state of a high temperature in a step of electrically connecting the package and the circuit board to each other with a solder. In a case where the temperature of the unit decreases after completion of this step, a warpage due to a bimetal effect occurs due to a difference in linear expansion coefficients of components of the unit.

In a case where the semiconductor chip is an imaging sensor chip, a flatness of a light receiving surface of the imaging sensor chip cannot be ensured due to a warpage caused by a bimetal effect. In a case where the light receiving surface warps in this way, a focus shifts around the light receiving surface, which affects an image quality. In a case where a size of the imaging sensor chip is large, it is particularly important to take measures against a warpage due to a bimetal effect. JP2002-100704A, JP2001-127200A, and JP2009-094168A do not recognize such a problem of the warpage of the imaging sensor chip.

The present invention has been made in view of the above circumstances, and an object of the present invention is to provide an imager capable of improving an image quality by preventing a warpage of an imaging sensor chip, and an imaging device comprising the imager.

An imager of an embodiment of the present invention comprises: an imaging sensor chip; a fixing member to which the imaging sensor chip is fixed, and which is electrically connected to the imaging sensor chip and has a first linear expansion coefficient; and a circuit board that is fixed to the fixing member via a conductive member, in which the circuit board includes a first member having the first linear expansion coefficient and a second member having a second linear expansion coefficient smaller than the first linear expansion coefficient and larger than a linear expansion coefficient of a semiconductor substrate forming the imaging sensor chip, and a content of the second member in a back side portion which is a portion between an intermediate part between a first surface and a second surface and the second surface in the circuit board is greater than a content of the second member in a front side portion which is a portion between the intermediate part and the first surface in the circuit board, the first surface being a surface of the circuit board on a side where the fixing member is fixed and the second surface being a surface of the circuit board opposite to the first surface.

An imaging device of the embodiment of the present invention comprises the above-described imager.

According to the present invention, it is possible to provide an imager capable of improving an image quality by preventing a warpage of an imaging sensor, and an imaging device including the imager.

BRIEF DESCRIPTION OF THE DRAWINGS

FIG. 5 is a diagram showing a configuration of a verified circuit board 52.

FIG. 6 is a diagram showing a configuration of a verified circuit board 52.

FIG. 7 is a diagram showing a configuration of a verified circuit board 52.

DESCRIPTION OF THE PREFERRED EMBODIMENTS

Hereinafter, embodiments of the present invention will be described with reference to the drawings.

Figure 1:
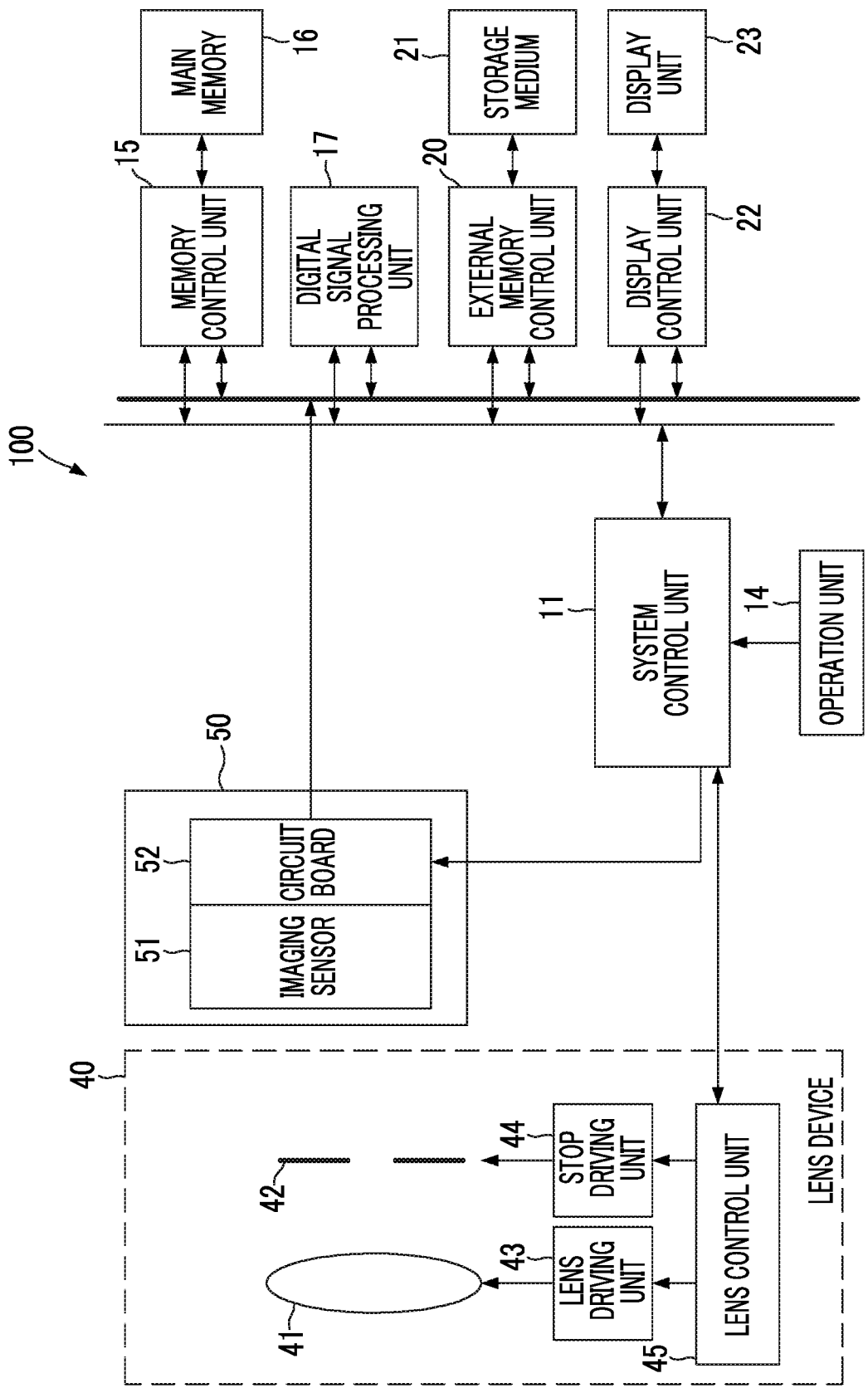
FIG. 1 is a diagram showing a schematic configuration of a digital camera 100 that is an embodiment of an imaging device of the present invention.

FIG. 1 is a diagram showing a schematic configuration of a digital camera 100 that is an embodiment of an imaging device of the present invention.

The digital camera 100 shown in FIG. 1 comprises a lens device 40 having an imaging lens 41, a stop 42, a lens driving unit 43, a stop driving unit 44, and a lens control unit 45.

The lens device 40 may be attachable and detachable to and from a main body of the digital camera 100, or may be integrated with the main body of the digital camera 100.

The imaging lens 41 includes a focus lens or a zoom lens that can move in an optical axis direction.

The lens control unit 45 of the lens device 40 is configured to be able to communicate with a system control unit 11 of the digital camera 100 by wire or wireless means.

According to a command from the system control unit 11, the lens control unit 45 changes a position of a principal point of the focus lens by driving the focus lens included in the imaging lens 41 via the lens driving unit 43, or controls the aperture amount of the stop 42 via the stop driving unit 44.

The digital camera 100 further comprises an imager 50 for imaging a subject through an imaging optical system, the system control unit 11, and an operation unit 14.

The imager 50 comprises an imaging sensor 51 such as a CCD image sensor or a CMOS image sensor, and a circuit board 52 on which the imaging sensor 51 is mounted.

The imaging sensor 51 has a light receiving surface (light receiving surface 10 in FIG. 3 which will be described later) in which a plurality of pixels are two-dimensionally arranged, and converts an image of the subject formed on the light receiving surface by the imaging optical system into an electric signal (pixel signal) by the plurality of pixels and outputs the electric signal.

The system control unit 11 drives the imaging sensor 51 to output the image of the subject captured through the imaging optical system of the lens device 40 as a captured image signal.

A command signal from a user is input to the system control unit 11 through the operation unit 14.

The system control unit 11 collectively controls the entire digital camera 100, and has a hardware structure of various processors that execute programs to perform processing.

The various processors include a central processing unit (CPU) that is a general-purpose processor executing a program to perform various types of processing, a programmable logic device (PLD) that is a processor of which a circuit configuration can be changed after manufacturing such as a field programmable gate array (FPGA), or a dedicated electric circuit that is a processor having a circuit configuration designed to be dedicated to executing specific processing such as an application specific integrated circuit (ASIC).

More specifically, structures of the various processors are electric circuits in which circuit elements such as semiconductor elements are combined.

The system control unit 11 may be constituted by one of the various processors, or may be constituted by a combination of two or more processors of the same type or different types (for example, a combination of a plurality of FPGAs or a combination of a CPU and an FPGA).

Further, an electric control system of the digital camera 100 comprises a main memory 16 constituted by a random access memory (RAM), a memory control unit 15 that controls data storage in the main memory 16 and data read out from the main memory 16, a digital signal processing unit 17 that performs digital signal processing on the captured image signal output from the imager 50 to generate captured image data according to various formats such as a joint photographic experts group (JPEG) format, an external memory control unit 20 that controls data storage in a storage medium 21 and data read out from the storage medium 21, a display unit 23 that is constituted by an organic electroluminescence (EL) display or a liquid crystal display, and a display control unit 22 that controls a display on the display unit 23.

Figure 2:
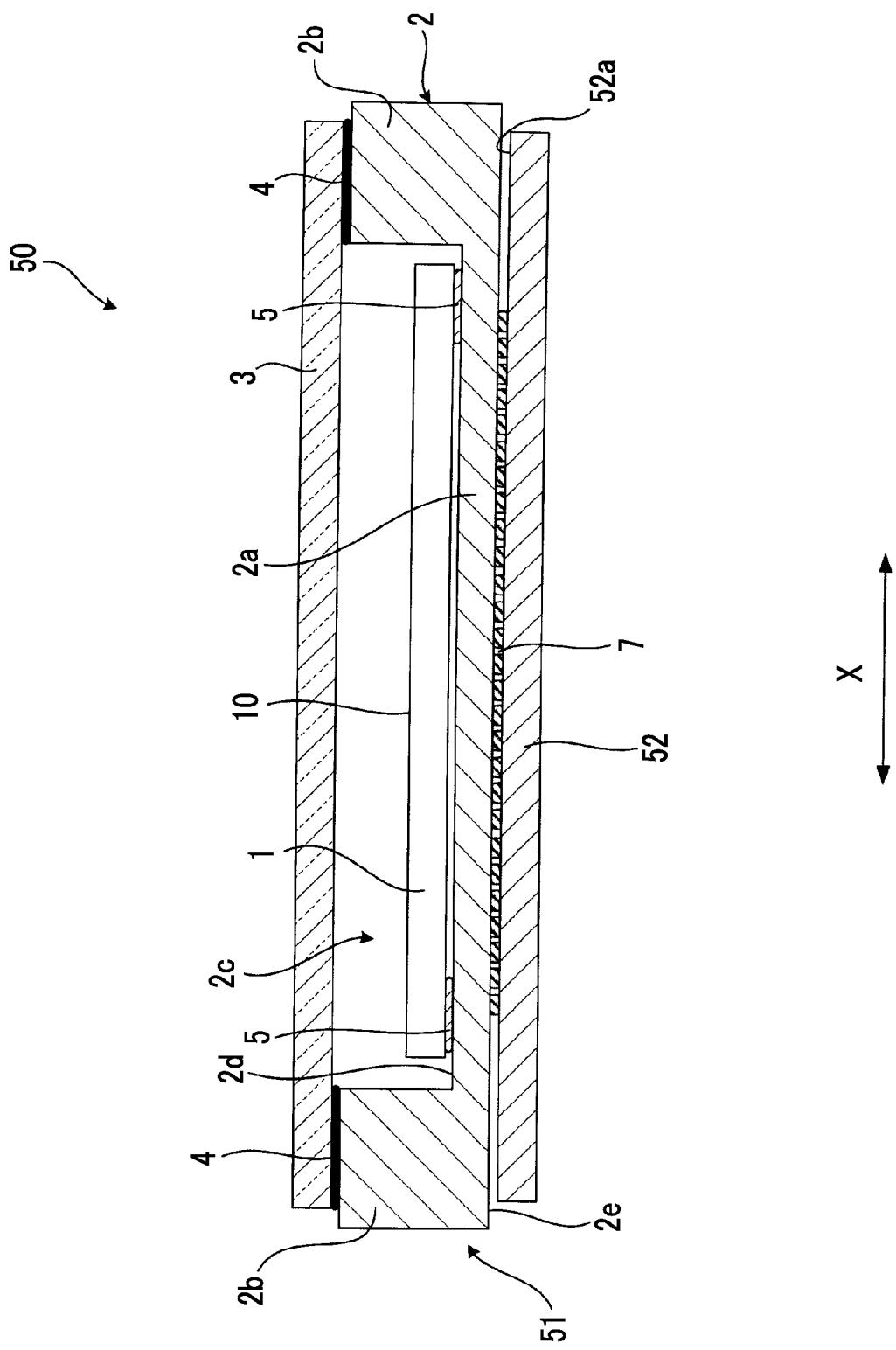
FIG. 2 is a schematic cross-sectional diagram of an imager 50 in the digital camera 100 shown in FIG. 1.

FIG. 2 is a schematic cross-sectional diagram of the imager 50 in the digital camera 100 shown in FIG. 1.

As shown in FIG. 2, the imager 50 comprises the imaging sensor 51 and the circuit board 52 fixed to a rear surface of the imaging sensor 51.

The imaging sensor 51 comprises a package 2 that has a bottom portion 2a having a plate shape such as a rectangular plate shape or a circular plate shape and a wall portion 2b erected at an end of the bottom portion 2a and having a frame shape such as a rectangular frame shape or a circular frame shape. The package 2 is configured to have a concave portion 2c in a portion surrounded by the wall portion 2b.

The imaging sensor 51 further comprises an imaging sensor chip 1 fixed to a bottom surface 2d of the concave portion 2c of the package 2, and a protective cover 3 constituted by a light-transmissive member such as a resin or a glass, which is fixed to an upper surface of the wall portion 2b of the package 2 with an adhesion material 4 and seals the imaging sensor chip 1 by closing the concave portion 2c of the package 2. The package 2 forms a fixing member.

The imaging sensor chip 1 is a semiconductor chip including a photoelectric conversion element such as a photodiode, and a light receiving surface 10 on which a readout circuit that converts charges accumulated in the photoelectric conversion element into signals and read out the signals is formed. The imaging sensor chip 1 has a rectangular planar shape and is fixed to the bottom surface 2d of the package 2 by an adhesion member 5 such as a resin used as a die bonding material. A semiconductor substrate of the imaging sensor chip 1 is made of, for example, silicon.

The package 2 is constituted by an insulating material such as alumina ceramic, or has a multilayer structure in which a conductive layer consisting of a conductive member such as tungsten and an insulating layer consisting of an insulating material such as alumina ceramic are laminated.

A large number of terminals (not shown) are formed on the bottom surface 2d of the concave portion 2c of the package 2, and these terminals are electrically connected to electrode pads formed on the imaging sensor chip 1 by conductive wires (not shown). Further, first terminals that are electrically connected to the terminals formed on the bottom surface 2d of the concave portion 2c of the package 2 are exposed on the rear surface 2e of the package 2 opposite to the side to which the protective cover 3 is fixed.

The circuit board 52 is adhered and fixed to the rear surface 2e of the package 2 by a plurality of conductive members 7. The conductive member 7 is in contact with each of the plurality of first terminals exposed on the rear surface 2e of the package 2.

The conductive member 7 may be constituted by a conductive material having an adhesion function, and for example, a solder consisting of an alloy of lead and tin or a solder consisting of an alloy of tin and copper is used.

The circuit board 52 is a plate-shaped member. On the circuit board 52, a circuit for driving the imaging sensor chip 1, a circuit for processing a signal output from the imaging sensor chip 1, and the like are formed. On a first surface 52a of the circuit board 52 on the side fixed to the package 2, terminals (second terminals) of these circuits are formed at positions in contact with the conductive member 7.

Therefore, the second terminal of the circuit included in the circuit board 52 and the first terminal formed on the rear surface of the package 2 are electrically connected to each other by the conductive member 7.

The circuit board 52 includes a first portion formed by an insulating layer consisting of an insulating material such as ceramic, and a second portion formed by a conductive layer consisting of a conductive material such as tungsten.

Figure 3:
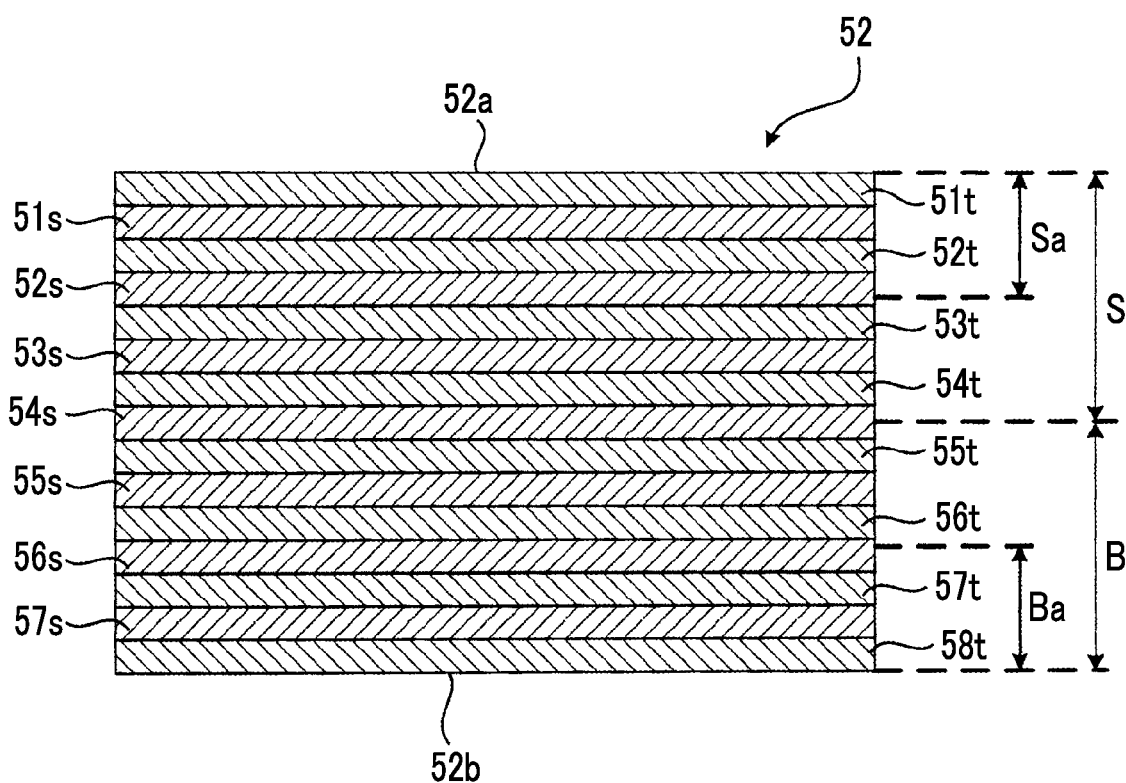
FIG. 3 is a schematic partial cross-sectional diagram showing a configuration example of a circuit board 52 shown in FIG. 2.

FIG. 3 is a schematic partial cross-sectional diagram showing a configuration example of the circuit board 52 shown in FIG. 2.

The circuit board 52 has a configuration in which between the first surface 52a on the side where the package 2 is fixed and a second surface 52b opposite to the first surface 52a, a conductive layer 51t, an insulating layer 51s, a conductive layer 52t, an insulating layer 52s, a conductive layer 53t, an insulating layer 53s, a conductive layer 54t, an insulating layer 54s, a conductive layer 55t, an insulating layer 55s, a conductive layer 56t, an insulating layer 56s, a conductive layer 57t, an insulating layer 57s, and a conductive layer 58t are laminated in this order from the first surface 52a to the second surface 52b.

The insulating layers 51s to 57s form a first member. The conductive layers 51t to 58t form a second member.

A linear expansion coefficient of each of the insulating layers 51s to 57s is the same as a linear expansion coefficient (first linear expansion coefficient) of the package 2. The fact that the two linear expansion coefficients are the same means that a difference between the two linear expansion coefficients is as small as, for example, a decimal point in addition to a case where the two linear expansion coefficients completely match with each other.

For example, by using ceramic (linear expansion coefficient=7.1 [ppm/° C.]) as the material of the package 2 and using ceramic as the insulating layers 51s to 57s of the circuit board 52, the linear expansion coefficient of each of the insulating layers 51s to 57s can be the same as the linear expansion coefficient of the package 2.

A linear expansion coefficient of each of the conductive layers 51t to 58t is smaller than the linear expansion coefficient of each of the insulating layers 51s to 57s, and is larger than a linear expansion coefficient of the semiconductor substrate forming the imaging sensor chip 1.

For example, silicon (linear expansion coefficient=3 [ppm/° C.]) is used as the semiconductor substrate forming the imaging sensor chip 1, ceramic (linear expansion coefficient=7.1 [ppm/° C.]) is used as the insulating layers 51s to 57s, and tungsten (linear expansion coefficient=4.5 [ppm/° C.]) is used as the conductive layers 51t to 58t. Thus, the above condition can be satisfied.

The linear expansion coefficient in the present specification indicates a change in length in a direction along the light receiving surface 10 of the image element 51.

In FIG. 3, a portion between an intermediate part between the first surface 52a and the second surface 52b and the second surface 52b in the circuit board 52 is shown as a back side portion B. A portion between the intermediate part and the first surface 52a in the circuit board 52 is shown as a front side portion S. Further, a portion on the second surface 52b side in a case where the back side portion B is divided into two in a direction in which the first surface 52a and the second surface 52b are arranged is shown as a back surface-25% thickness portion Ba. A portion on the first surface 52a side in a case where the front side portion S is divided into two in a direction in which the first surface 52a and the second surface 52b are arranged is shown as a front surface-25% thickness portion Sa.

A proportion of the total amount of the conductive layers 55t, 56t, 57t, and 58t in the back side portion B of the circuit board 52 in the total amount (hereinafter, referred to as the whole amount) of the conductive layers 51t to 58t included in the whole circuit board 52 (hereinafter, referred to as a back side content) is greater than a proportion of the total amount of the conductive layers 51t, 52t, 53t, and 54t in the front side portion S of the circuit board 52 in the whole amount (hereinafter, referred to as a front side content).

Furthermore, a proportion of the total amount of the conductive layers 57t and 58t in the back surface-25% thickness portion Ba of the circuit board 52 in the whole amount (hereinafter, referred to as a back surface-25% thickness content) is greater than a proportion of the total amount of the conductive layers 51t and 52t in the front surface-25% thickness portion Sa of the circuit board 52 in the whole amount (hereinafter, referred to as a front surface-25% thickness content).

A relationship between the back side content and the front side content may be such that the back side content is greater than the front side content, but the back side content is preferably 1.2 times or more the front side content. The back side content is preferably 1.5 times or more the front side content.

In a case where the back side content is greater than the front side content, it is not essential that the back surface-25% thickness content is greater than the front surface-25% thickness content. However, it is preferable that the back surface-25% thickness content is greater than the front surface-25% thickness content. The back surface-25% thickness content is more preferably 1.2 times or more, and still more preferably 1.5 times or more the front surface-25% thickness content.

Figure 4:
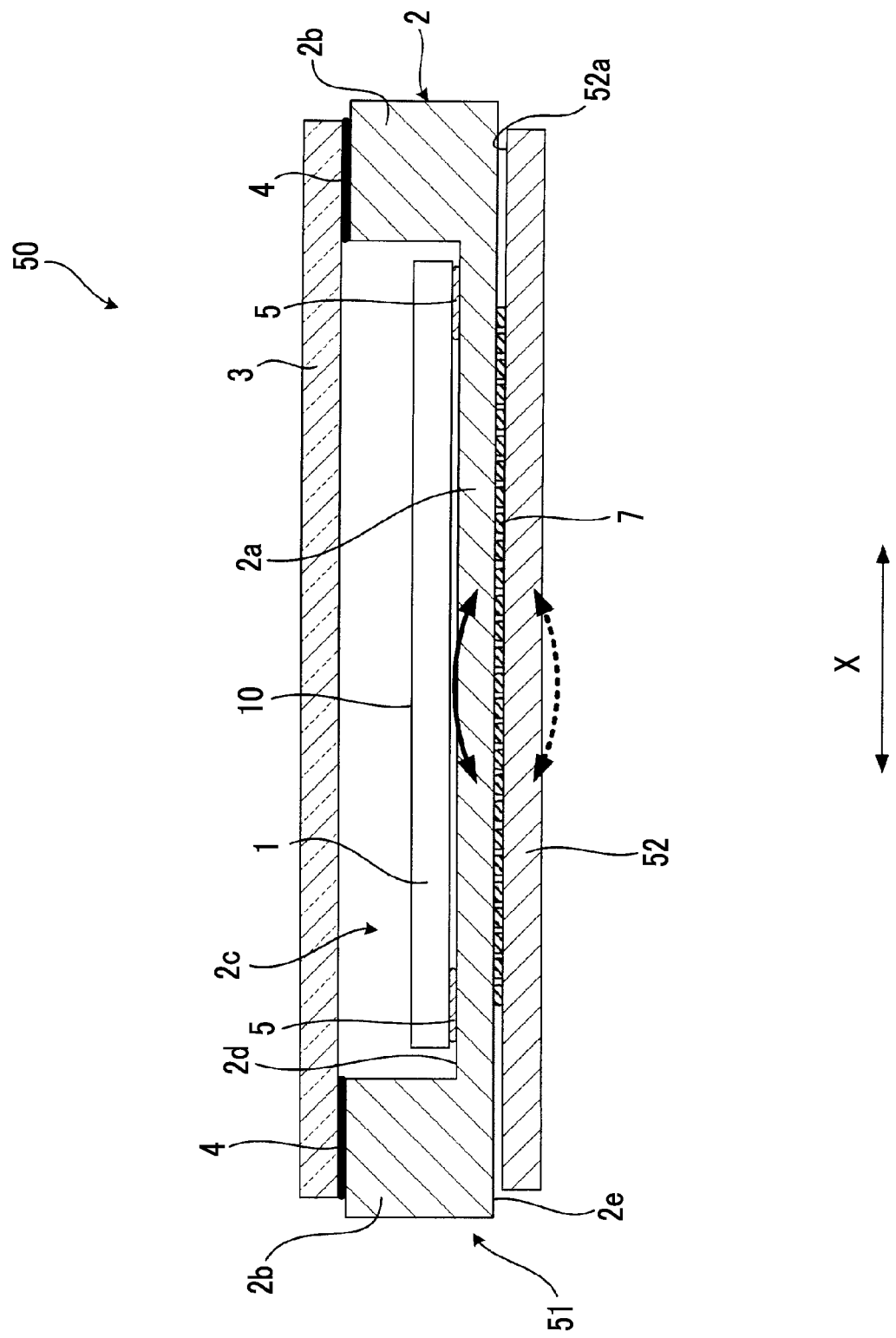
FIG. 4 is a schematic diagram for illustrating a warpage state of the imager 50 shown in FIG. 2.

In the imager 50 configured as described above, the linear expansion coefficient of the imaging sensor chip 1 is smaller than the linear expansion coefficient of the package 2. Therefore, as shown in FIG. 4, the imaging sensor chip 1 and the package 2 may be warped in a direction indicated by a solid arrow due to a bimetal effect.

On the other hand, since the package 2 and the circuit board 52 have the same linear expansion coefficient, no warpage due to a difference in the linear expansion coefficient between the package 2 and the circuit board 52 occurs. However, in the circuit board 52, the back side content is greater than the front side content. Therefore, in the circuit board 52 alone, as indicated by a dotted arrow in FIG. 4, a warpage occurs in a direction opposite to a direction of a warpage of the imaging sensor chip 1 and the package 2 due to a difference between the back side content and the front side content. As a result, the warpage of the imaging sensor chip 1 and the package 2 is canceled by the warpage of the circuit board 52, and the warpage of the imaging sensor chip 1 and the package 2 can be reduced.

In particular, in a case where the back surface-25% thickness content is greater than the front surface-25% thickness content, the warpage of the circuit board 52 is likely to occur, and thus the warpage of the imaging sensor chip 1 and the package 2 is more effectively reduced.

Next, results obtained by verifying the effect of the above-described configuration of the circuit board 52 by simulation will be described. In the simulation, in the imager 50, the material of the package 2 was ceramic and tungsten, the material of the conductive layer of the circuit board 52 shown in FIG. 3 was tungsten, the material of the insulating layer of the circuit board 52 shown in FIG. 3 was ceramic, and the content of each conductive layer of the circuit board 52 in the whole amount was set as shown in FIGS. 5 to 7.

FIG. 5 shows a verification example in which the back side content is 60%, the front side content is 40%, the back surface-25% thickness content is 30%, and the front surface-25% thickness content is 20%.

FIG. 6 shows a verification example in which the back side content is 55%, the front side content is 45%, the back surface-25% thickness content is 27.5%, and the front surface-25% thickness content is 22.5%.

FIG. 7 shows a reference verification example in which the back side content is 35% and the front side content is 65%.

For the examples of FIGS. 5 to 7, verification was performed under a first condition that the whole amount of the conductive layers included in the circuit board 52 was the same as the whole amount of the conductive layers included in the package 2 and a second condition that it was smaller than the whole amount of the conductive layers included in the package 2 by about 2%.

As results obtained by simulating the amount of a warpage at an image height position of 80% on the light receiving surface 10 of the imaging sensor chip 1, in the reference verification example of FIG. 7, the amount of a warpage was 13.54 μm under the first condition, and the amount of a warpage was 15.08 μm under the second condition.

In the verification example of FIG. 6, the amount of a warpage was 10.08 μm under the first condition, and the amount of a warpage was 11.96 μm under the second condition.

In the verification example of FIG. 5, the amount of a warpage was 8.83 μm under the first condition, and the amount of a warpage was 10.8 μm under the second condition.

In a case where the amount of a warpage at the image height position of 80% on the light receiving surface 10 is 12 μm or less, there is no practical problem. In the verification examples of FIGS. 5 and 6, the amount of a warpage is 12 μm or less, whereas in the reference verification example of FIG. 7, the amount of a warpage exceeds 12 μm. This result also shows that the warpage of the imaging sensor chip 1 can be reduced since the back side content is greater than the front side content.

Further, in the verification example of FIG. 5 and the verification example of FIG. 6, the amount of a warpage of the verification example of FIG. 5 is relatively small. This result shows that the amount of a warpage of the imaging sensor chip 1 can be further reduced by increasing the back side content.

As described above, the following items are described in the present specification.

(1)

An imager comprising:

an imaging sensor chip;

a fixing member to which the imaging sensor chip is fixed, and which is electrically connected to the imaging sensor chip and has a first linear expansion coefficient; and a circuit board that is fixed to the fixing member via a conductive member, in which the circuit board includes a first member having the first linear expansion coefficient and a second member having a second linear expansion coefficient smaller than the first linear expansion coefficient and larger than a linear expansion coefficient of a semiconductor substrate forming the imaging sensor chip, and a content of the second member in a back side portion which is a portion between an intermediate part between a first surface and a second surface and the second surface in the circuit board is greater than a content of the second member in a front side portion which is a portion between the intermediate part and the first surface in the circuit board, the first surface being a surface of the circuit board on a side where the fixing member is fixed and the second surface being a surface of the circuit board opposite to the first surface.

(2)

The imager according to (1), in which a content of the second member in a portion on the second surface side in a case where the back side portion of the circuit board is divided into two in a direction in which the first surface and the second surface are arranged is greater than a content of the second member in a portion on the first surface side in a case where the front side portion of the circuit board is divided into two in the direction.

(3)

The imager according to (2), in which the content of the second member in the portion on the second surface side of the back side portion is 1.2 times or more the content in the portion on the first surface side of the front side portion.

(4)

The imager according to (3), in which the content of the second member in the portion on the second surface side of the back side portion is 1.5 times or more the content in the portion on the first surface side of the front side portion.

(5)

The imager according to any one of (1) to (4), in which the content of the second member in the back side portion is 1.2 times or more the content of the second member in the front side portion.

(6)

The imager according to (5), in which the content of the second member in the back side portion is 1.5 times or more the content of the second member in the front side portion.

(7)

An imaging device comprising:

the imager according to any one of (1) to (6).

Although various embodiments have been described with reference to the drawings, it goes without saying that the present invention is not limited to such examples. It is obvious that a person skilled in the art is able to find various modification examples and adjustment examples within the scope of the appended claims, and it should be understood that these modification examples and adjustment examples naturally belong to the technical scope of the present invention. Further, the components according to the above-described embodiment may be optionally combined with each other, without departing from the spirit of the invention.

This application is based on Japanese Patent Application filed on Feb. 22, 2018 (JP2018-030137), the content of which is incorporated herein by reference.

The present invention is highly convenient and effective to be applied to an electronic device having an imaging function, such as a digital camera, a smartphone, a tablet terminal, a personal computer, a robot, or an endoscope.

EXPLANATION OF REFERENCES

100: digital camera
11: system control unit
14: operation unit
41: imaging lens
42: stop
43: lens driving unit
44: stop driving unit
45: lens control unit
50: imager
51: imaging sensor
52: circuit board
15: memory control unit
16: main memory
17: digital signal processing unit
20: external memory control unit
21: storage medium
22: display control unit
23: display unit
1: imaging sensor chip 2: package
2a: bottom portion
2b: wall portion
2c: concave portion
2d: bottom surface
2e: rear surface
3: protective cover
4: adhesion material
5: adhesion member
7: conductive member
10: light receiving surface
52: circuit board
52a: first surface
52b: second surface
51t to 58t: conductive layer
51s to 57s: insulating layer
S: front side portion
Sa: front surface-25% thickness portion
B: back side portion
Ba: back surface-25% thickness portion

What is claimed is:

1. An imager comprising:
an imaging sensor chip;
a fixing member to which the imaging sensor chip is fixed, and which is electrically connected to the imaging sensor chip and has a first linear expansion coefficient; and
a circuit board that is fixed to the fixing member via a conductive member,
wherein the circuit board comprises a first member having the first linear expansion coefficient and a second member having a second linear expansion coefficient smaller than the first linear expansion coefficient and larger than a linear expansion coefficient of a semiconductor substrate forming the imaging sensor chip, and
a content of the second member in a back side portion which is a portion of the circuit board between an intermediate part between a first surface and a second surface and the second surface in the circuit board is greater than a content of the second member in a front side portion which is a portion of the circuit board between the intermediate part and the first surface in the circuit board, the first surface being a surface of the circuit board on a side where the fixing member is fixed and the second surface being a surface of the circuit board opposite to the first surface.

2. The imager according to claim 1,
wherein a content of the second member in a portion of the back side portion on the second surface side in a case where the back side portion of the circuit board is divided into two in a direction in which the first surface and the second surface are arranged is greater than a content of the second member in a portion of the front side portion on the first surface side in a case where the front side portion of the circuit board is divided into two in the direction.

3. The imager according to claim 2,
wherein the content of the second member in the portion of the back side portion on the second surface side is 1.2 times or more the content of the second member in the portion of the front side portion on the first surface side.

4. The imager according to claim 3,
wherein the content of the second member in the portion of the back side portion on the second surface side is 1.5 times or more the content of the second member in the portion of the front side portion on the first surface side.

5. The imager according to claim 1,
wherein the content of the second member in the back side portion is 1.2 times or more the content of the second member in the front side portion.

6. The imager according to claim 2,
wherein the content of the second member in the back side portion is 1.2 times or more the content of the second member in the front side portion.

7. The imager according to claim 3,
wherein the content of the second member in the back side portion is 1.2 times or more the content of the second member in the front side portion.

8. The imager according to claim 4,
wherein the content of the second member in the back side portion is 1.2 times or more the content of the second member in the front side portion.

9. The imager according to claim 5,
wherein the content of the second member in the back side portion is 1.5 times or more the content of the second member in the front side portion.

10. The imager according to claim 6,
wherein the content of the second member in the back side portion is 1.5 times or more the content of the second member in the front side portion.

11. The imager according to claim 7,
wherein the content of the second member in the back side portion is 1.5 times or more the content of the second member in the front side portion.

12. The imager according to claim 8,
wherein the content of the second member in the back side portion is 1.5 times or more the content of the second member in the front side portion.

13. An imaging device comprising:
the imager according to claim 1.

* * * * *